(12) United States Patent
Breivik et al.

(10) Patent No.: US 9,409,851 B2
(45) Date of Patent: Aug. 9, 2016

(54) LONG CHAIN MONOUNSATURATED FATTY ACID COMPOSITION AND METHOD FOR THE PRODUCTION THEREOF

(71) Applicant: EPAX NORWAY AS, Aalesund (NO)

(72) Inventors: Harald Breivik, Inndyr (NO); Tanja Vojnovic, Porsgrunn (NO)

( * ) Notice: Subject to any disclaimer, the term of this patent is extended or adjusted under 35 U.S.C. 154(b) by 0 days.

(21) Appl. No.: 14/666,975

(22) Filed: Mar. 24, 2015

(65) Prior Publication Data

US 2015/0284312 A1    Oct. 8, 2015

Related U.S. Application Data

(60) Provisional application No. 61/976,180, filed on Apr. 7, 2014.

(51) Int. Cl.
*C11B 7/00* (2006.01)
*C07C 57/03* (2006.01)
*C07C 51/47* (2006.01)

(52) U.S. Cl.
CPC ............ *C07C 57/03* (2013.01); *C07C 51/47* (2013.01); *C11B 7/0008* (2013.01); *C11B 7/0025* (2013.01)

(58) Field of Classification Search
CPC ...... C07C 57/03; C07C 57/47; C11B 7/0008; C11B 7/0025
USPC ........................................ 554/199
See application file for complete search history.

(56) References Cited

U.S. PATENT DOCUMENTS

| 5,917,068 A | 6/1999 | Barnicki et al. |
| 8,586,772 B2 | 11/2013 | Harting Glade et al. |
| 2013/0150602 A1 | 6/2013 | Kelliher et al. |

OTHER PUBLICATIONS

Tor-Chern Chen, et al.: "Enrichment of eicosapentaenoic acid and docosahexaenoic acid in saponified menhaden oil", Journal of the American Oil Chemists' Society (JAOCS), Springer, DE, vol. 77, No. 4, Apr. 1, 2000, pp. 425-428, XP002588209.
Ault et al; *Some Observations Concerning the Chemistry of Arahidonic Acid and Its Quantitative Estimation*; J. Biol. Chem. 1934 107: 615-622.
Silk et al; *South African Pilchard Oil. 2. Concentrates of highly unsaturated fatty acids and alcohols derived from South African Pilchard Oil*; Biochem, Feb. 1954; 57(4): 574-577.
Tsujimoto et al, *Method for the Separation of Highly Unsaturated Fatty Acids in Fish Oil*, J. Chem. Ind., Tokyo, 1920, 23 (272).
Edisbury et al, *The Absorption Spectra of Acids from Fish-Liver Oils*, Biochem J. Apr. 1935; 29(4): 899-908.
Imamura et al, *Long-chain monounsaturated Fatty acids and incidence of congestive heart failure in 2 prospective cohorts*, Circulation Apr. 9, 2013;127(14):1512-21.
Yang et al; *Dietary supplementation with long-chain monounsaturated fatty acids attenuates obesity-related metabolic dysfunction and increases expression of PPAR gamma in adipose tissue in type 2 diabetic KK-Ay mice*; Nutrition & Metabolism, 2013, 10:16.
Hlias et al; *Combined fish oil and high oleic sunflower oil supplements neutralize their individual effects on the lipid profile of healthy men*, Lipids. Sep. 2013;48(9):853-61.
Opstvedt, *Fish Lipids in Animal Nutrition*, Informa Technical Bulletin, No. 22 Oct. 1985.
Fontell et al, *Some new methods for separation and analysis of fatty acids and other lipids*, J Lipid Res. Oct. 1960;1:391-404.
Haraldsson et al, *Separation of eicosapentaenoic acid and docosahexaenoic acid in fish oil by kinetic resolution using lipase*, Journal of the American Oil Chemists' Society 75 (11), 1551-1556.

*Primary Examiner* — Deborah D Carr

(57) ABSTRACT

In one aspect, the present invention is directed to a method for obtaining an enriched composition of long chain monounsaturated fatty acids from an oil composition, typically a fish oil composition, comprising both long chain monounsaturated fatty acids and long chain polyunsaturated fatty acids. In another aspect, the present invention is directed to a composition comprising at least 70% by weight of long chain monounsaturated fatty acids.

20 Claims, No Drawings

LONG CHAIN MONOUNSATURATED FATTY ACID COMPOSITION AND METHOD FOR THE PRODUCTION THEREOF

FIELD OF THE INVENTION

In one aspect, the present invention is directed to a method for obtaining an enriched composition of long chain monounsaturated fatty acids from an oil composition, typically a fish oil composition, comprising both long chain monounsaturated fatty acids and long chain polyunsaturated fatty acids. In another aspect, the present invention is directed to a composition comprising at least 70% by weight of long chain monounsaturated fatty acids.

BACKGROUND OF THE INVENTION

Although the consumption of long chain polyunsaturated fatty acids such as docosahexaenoic acid (DHA) and eicosapentaenoic acid (EPA) has long been recognized as providing a variety of health benefits, until very recently the consumption of their monounsaturated equivalents was thought to be unhealthy. As is stated by Imamura et al, "*Long-chain monounsaturated fatty acids and incidence of congestive heart failure in two prospective cohorts*", Circulation, 2013 Apr. 9; 127(14): 1512-1522, "In the 1960s-1980s, feeding experiments in rodents, pigs and non-human primates suggested that consumption of erucic acid (22:1n9) and cetoleic acid (22:1n11) caused cardiac steatosis. Although potential effects in humans were never studied, mechanistic studies suggest that exposure to long-chain monounsaturated fatty acids (LCMUFA. 20:1, 22:1 and 24:1 fatty acids) might impair myocardium". In this regard, it is noted that lipids are described by the formula X:YnZ wherein X is the number of carbon atoms in their alkyl chain, and Y is the number of double bonds in such chain; and where "Z" is the number of carbon atoms from the methyl end group to the first double bond. In nature the double bonds are all in the cis-form. In polyunsaturated fatty acids each double bond is separated from the next by one methylene ($-CH_2-$) group. Using this nomenclature, EPA is 20:5n3 while DHA is 22:6n3.

After analyzing circulating phospholipid LCMUFA content in patients exhibiting arteriosclerosis or congestive heart failure, Imamura found that increased levels of 24:1 are associated with specific physiologic risk factors as well as with higher incidence of congestive heart failure. Consumption of 22:1 led to some increased risk (as 22:1 is elongated to 24:1); no association was found with respect to 20:1 fatty acids.

Recent research has shown that 20:1 and 22:1 long-chain monounsaturated fatty acids actually possess desirable health effects. Thus Yang et al, *Dietary supplementation with long-chain monounsaturated fatty acids attenuates obesity-related metabolic dysfunction and increases expression of PPAR gamma in adipose tissue in type 2 diabetic KK-A$^y$ mice*, Nutrition & Metabolism 2013, 10:16 discloses that the dietary treatment of such mice with such long-chain monounsaturated fatty acids improved their diabetic condition.

Unfortunately, recent research has also indicated that combining higher long-chain polyunsaturated fatty acids (LC-PUFAs) such as EPA (20:5) and DHA (22:6) from fish oil with certain monounsaturated fatty acids, such as oleic acid (18:1), from plants may cancel out the health benefits derived from each. Thus Hlais et al, *Combined Fish Oil and High Oleic Sunflower Oil Supplements Neutralize the Individual Effects on the Lipid Profile of Healthy Men*, Lipids (2013) 48:853-861 conclude that "the impact of oleic acid (n-9) on total and LDL cholesterol was altered by the addition of fish oil (n-3). These effects may have been the result of enzymatic competition between the two types of fatty acids." (Abstract).

Accordingly, it would be desirable to possess a composition comprising a high concentration of higher long-chain monounsaturated fatty acids (i.e., 20:1 and 22:1), which composition did not contain a substantial amount of higher long-chain polyunsaturated fatty acids as well. One difficulty associated with the production of such a material is that many of the fish species which produce oil having a higher concentration of such higher long-chain monounsaturated fatty acids (for example herring) also produce high concentrations of higher long-chain polyunsaturated fatty acids as well. Interestingly, the reverse is not true—most higher long-chain polyunsaturated fatty acids such as EPA and DHA are isolated from species of fish (primarily anchovy, found off the Western coast of South America) which produce oils having a high long-chain polyunsaturated fatty acid content and a low content of long-chain monounsaturated fatty acids. Thus, for example, Opstvedt, *Fish Lipids in Animal Nutrition*, Norwegian Herring Oil & Meal Industry Research Industry, Technical Bulletin No. 22, October 1985 reports that Peruvian Anchovy has a 20:5 and 22:6 content of 33.7 (w/w %), but a 20:1+22:1 content of only 2.8%.

Unfortunately, many of the processes typically employed to concentrate fish oil fatty acids, such as short path distillation and supercritical fluid extraction primarily separate fatty acid derivatives based upon variation in chain length rather than saturation. While fractionation methods such as urea fractionation may be employed, such processes are economically unacceptable due to the large amounts of reagent needed, particularly with fish oils which contain large amounts of both long-chain polyunsaturated fatty acids and long-chain monounsaturated fatty acids.

Lithium salts have been employed to separate long-chain polyunsaturated fatty acids from other components of fish oil in the past. Thus, for example, US Patent Application 2013/0150602 (Keliher et al) discloses a process where lithium salts are employed to remove non-acidic impurities from a single fatty acid—rather than separating fatty acids from one another. The non-acidic impurities are typically impurities that are produced during a chemical synthesis of a single fatty acid (see paragraph 44 of 2013/0150602). WO 2011/095284 (Horlacher et al) discloses a process wherein saturated fatty acids are removed from polyunsaturated fatty acids (particularly EPA and DHA) by treating free fatty acids concentrated from fish oils having a high EPA and DHA content with a sodium or lithium salt and ethanol. While the prior art discloses that a lithium salt/acetone fractionation process could be employed, such art indicates that the use of such a process would not be particularly effective. Thus, Fontell et al, *Some new method for separation and analysis of fatty acids and other lipids*, Journal of Lipid Research, Volume 1, Number 5, pages 391-404 (1960) state (on pages 391-392) that "One inherent disadvantage of the method [lithium salt/acetone fractionation] is the co-crystallization of fatty acids, which leads to less perfect separations than solubility data would predict. While it is normally possible to obtain quite good separation of saturated from unsaturated fatty acids by this method, a separation of monoene from polyene acids is less precise . . ."

Accordingly, it is completely unexpected that a lithium fractionation employing an organic solvent such as ethanol and/or acetone could be used to separate long-chain monounsaturated fatty acids from long-chain polyunsaturated fatty acids in compositions comprising a high concentration of both such materials.

SUMMARY OF THE INVENTION

In one aspect, the present invention is directed to a method for obtaining an enriched composition of $C_{20}$-$C_{22}$ long chain monounsaturated fatty acids comprising the steps of:

a) Mixing an oil composition comprising $C_{20}$-$C_{22}$ long chain polyunsaturated fatty acids and at least 15% by weight $C_{20}$-$C_{22}$ long chain monounsaturated fatty acids with (i) an organic solvent selected from the group consisting of $C_1$-$C_5$ alcohols and ketones of the formula $R^1(C=O)R^2$ wherein $R^1$ and $R^2$ are each independently $C_1$-$C_5$ alkyl; and (ii) a lithium salt to form a mixed composition comprising the lithium salts of long chain monounsaturated fatty acids and the lithium salts of the long chain polyunsaturated fatty acids at 15° C. to 80° C.;

b) Reducing the temperature of the mixed composition formed in step a such that the lithium salts of the long chain monounsaturated fatty acids form a precipitate; and c) Removing the precipitate to obtain an enriched composition of long chain monounsaturated fatty acids.

In another aspect, the present invention is directed to a composition comprising at least 70% by weight of $C_{20}$-$C_{22}$ long chain monounsaturated fatty acids.

DETAILED DESCRIPTION OF THE INVENTION

In one aspect, the present invention is directed to a method for obtaining an enriched composition of $C_{20}$-$C_{22}$ long chain monounsaturated fatty acids comprising the steps of:

a) Mixing an oil composition comprising $C_{20}$-$C_{22}$ long chain polyunsaturated fatty acids and at least 15% by weight $C_{20}$-$C_{22}$ long chain monounsaturated fatty acids with (i) an organic solvent selected from the group consisting of $C_1$-$C_5$ alcohols and ketones of the formula $R^1(C=O)R^2$ wherein $R^1$ and $R^2$ are each independently $C_1$-$C_5$ alkyl; and (ii) a lithium salt to form a mixed composition comprising the lithium salts of long chain monounsaturated fatty acids and the lithium salts of the long chain polyunsaturated fatty acids at 15° C. to 80° C.;

b) Reducing the temperature of the mixed composition formed in step a such that the lithium salts of the long chain monounsaturated fatty acids form a precipitate; and c) Removing the precipitate to obtain an enriched composition of long chain monounsaturated fatty acids.

As is employed herein, the term "long chain monounsaturated fatty acid" or "LC-MUFA" refers to a fatty acid having 20 to 22 carbon atoms and a single double bond in their alkyl chains (20:1 to 22:1 fatty acids). Similarly, the term "long chain polyunsaturated fatty acid" or "LC-PUFA" refers to a fatty acid having 20 to 22 carbon atoms and more than one double bond in their alkyl chains.

Further, as is employed herein, the term "oil composition" means an oil itself (e.g., a fish oil) or a material derived from such oil (by treatments such as ethylation, short path distillation and/or supercritical fluid extraction) which comprises at least 15% by weight LC-MUFA.

The oil composition starting material may be derived from any source having an LC-MUFA content of at least 15% by weight. Typically, such oil composition will contain a significant LC-PUFA content (e.g., of 5% by weight or more). Such oil may be derived from fish, crustaceans such as hill, algae, plankton, higher plants, or any other source. Preferred fish species include herring, capelin, mackerel, blue whiting, sand eel, cod viscera and pollock viscera.

The starting material may comprise oil, free fatty acids (e.g., hydrolyzed fish oil), monoesters such as ethyl esters or mixtures thereof. As at any given carbon chain length the lithium salts of saturated fatty acids are less soluble in the organic solvent than the lithium salts of the corresponding monounsaturated fatty acids, a first fractionation step may be performed in order to reduce the content of saturated fatty acids (such as is illustrated in Examples 1 and 2 below). When monoesters such as ethyl esters or free fatty acids are employed, typically such starting material is subjected to a prior concentration step (such as short path distillation or supercritical fluid extraction) to remove shorter chain fatty acids from such composition. As the saturated fatty acids of fish oil have relatively short chain length (in herring oil mostly C14 and C16) such a procedure will also significantly reduce the content of saturated fatty acids in the starting material.

Free fatty acids may be formed from the oil by hydrolysis according to processes known to those of skill in the art, for example as shown by Gudmundur G. Haraldsson and Bjorn Kristinsson in J. Am. Oil Chem. Soc. (1998) 75:1551-1556. Monoesters such ethyl esters may formed employing processes well known to those of skill in the art, for example by reaction of the oil with the corresponding water-free alcohol using sodium alcoholate as a catalyst and removing the glycerol that is formed as a by-product, i.e. similar to known art for the production of bio-diesel or for the manufacture of commercially available omega-3 products.

Surprisingly, the process of the present invention works equally well on the mono esters (preferably ethyl esters) of the oil, and even directly on the oil itself. Moreover, it has been unexpectedly found that a process starting with esters can efficiently be carried out using a mixture of potassium and lithium hydroxide: The combined lithium and potassium content has to be sufficient to result in an in situ hydrolysis of the oil, while the content of the more expensive lithium hydroxide only has to be sufficient to obtain the desired degree of fractionation, i.e. obtain the desired degree of precipitation of fatty acids as lithium salts. As an alternative to potassium hydroxide other bases such as sodium hydroxide, magnesium hydroxide and the like may be used.

In step a of the present process, the oil composition is mixed with a lithium salt in the presence of an organic solvent to form a mixed composition comprising the lithium salts of long chain monounsaturated fatty acid and the lithium salts of the long chain polyunsaturated fatty acid.

Due to economic considerations, the lithium salt is preferably added in an amount just sufficient to precipitate the desired fractionation. When ethyl esters or oil are used as starting material, lithium salt is preferably added in an amount sufficient for the desired fractionation, and another base (such as potassium hydroxide) is added in an amount sufficient to obtain a complete hydrolysis of the oil. A benefit of using potassium hydroxide is that it can readily be dissolved both in ambient ethanol and water, adding flexibility in order to obtain the desired water content of the solvent without unnecessarily increasing the total solvent volume.

The organic solvent employed is selected from the group consisting of $C_1$-$C_5$ alcohols and ketones of the formula $R^1(C=O)R^2$ wherein $R^1$ and $R^2$ are each independently $C_1$-$C_5$ alkyl. Preferred organic solvents include acetone and ethanol. In certain embodiments, such organic solvent may be mixed with a minor amount (i.e., less than 50%, typically less than 25% by weight) of water. Such solvent is generally added an amount of between 0.5 and 8 liters, preferably between 1 and 4 liters, per kilogram of fish composition. In addition to the optional water content in the organic solvent, water may also be used as a solvent for the lithium hydroxide and/or potassium hydroxide and/or any other alkaline material that is used in order to perform hydrolysis and/or precipitation of fatty acids.

Lithium salts which may be employed include lithium carbonate, lithium bicarbonate and lithium hydroxide; with lithium hydroxide being preferred. The lithium salt may be employed as a hydrate, for example lithium hydroxide monohydrate. Such lithium salt(s) are typically employed in the form of an aqueous solution, although such salt may be added as a solid in the event that such salt is soluble in the particular organic solvent employed. Thus, for example, lithium hydroxide may be employed as a solid when ethanol is used as the organic solvent.

Employing the lithium salt of C20:1 as an example, lithium accounts for 2.2% of the weight of the salt. Accordingly, a relatively low weight of lithium salts is sufficient in order to obtain a desired fractionation. Depending on the desired fractionation, typically, such lithium salts are added in an amount of between 5 and 70 grams calculated as lithium per kilogram of oil composition; preferably, between 10 and 60 grams per kilogram of oil composition; more preferably between 10 and 40 grams per kilogram of oil composition of lithium salts are added. Due to the costs of such lithium salts, it may be commercially advantageous to employ such salts in combination with their corresponding potassium equivalent (for example, potassium hydroxide may be additionally added to the mixture).

The oil composition, lithium salt and organic solvent are blended until the lithium salts of long chain monounsaturated fatty acids and the lithium salts of the long chain polyunsaturated fatty acids are formed. Such blending may range from several minutes or less to several hours or more, depending upon factors such as: the volume and concentration of the components, the particular components selected, the extent of agitation employed, the temperature selected, and the like. Typically, the components are mixed at a temperature of between ambient temperature (i.e., about 15° C. or more) and 80° C. for a period of between a few minutes, especially in the case of free fatty acids as starting materials, and up to 24 hours; the longer times especially with ethyl esters and triglycerides as starting materials. When oil or ethyl esters thereof are employed as the starting material (as opposed to free fatty acids) longer mixing times are generally required to produce such lithium salts.

In step b of the process of the present invention, the mixed composition formed in step a is subjected to conditions such that the lithium salts of the long chain monounsaturated fatty acids form a precipitate. Typically, this involves cooling (or letting such composition cool) to a temperature of less than ambient, preferably 10° C. or less and even more preferably to about 0° C. or less. A larger amount of lithium salts will reduce the need to cool the reaction mixture to a very low temperature. An alternative procedure in order to remove the monounsaturated fatty acids would also be to remove the precipitate that is formed at a relative high temperature, for example at 10-15° C., and then to reduce the volume of the reaction mixture in one or more steps by suitable evaporative processes before removal of one or several further fractions of precipitate.

Once the precipitate comprising the lithium salts of long chain monounsaturated fatty acids has formed, the precipitate is separated from the solution, typically by filtering, to obtain a composition comprising lithium salts of long chain monounsaturated fatty acids and a filtrate comprising a concentrated solution of long chain polyunsaturated fatty acid.

The filtrate comprises a high concentration of the lithium salts of long chain polyunsaturated fatty acids which can be converted back into free fatty acids (and the lithium recovered) by treatment with an acid such as citric acid, hydrochloric acid or the like. The free LC-PUFAs formed can be further purified and recovered in concentrations of 80% by weight or higher, employing processes well known to those of ordinary skill in the art; and subsequently converted back into triglycerides employing enzyme or chemically catalyzed esterification with glycerol. Thus, the process of this invention enables the production of highly concentrated LC-PUFAs from fish or other oils which are typically not employed as starting materials due to their high LC-MUFA and relatively low LC-PUFA contents, and thus provides enhanced flexibility in the choice of starting materials in the event that sufficient supplies of those fish species which are typically employed to produce such highly concentrated LC-PUFA compositions are not readily available.

The precipitate may optionally be purified by recrystallization employing a solvent such as ethanol. Such (optionally purified) LC-MUFA composition is converted into a free fatty acid by treatment with an acid such as citric acid, hydrochloric acid, phosphoric acid, sulfuric acid and the like. The free LC-MUFAs formed can be further purified and recovered in concentrations of 70% by weight or higher, employing processes well known to those of ordinary skill in the art; and subsequently converted back into triglycerides employing enzyme catalyzed esterification with glycerol. In other embodiments, the free long chain monounsaturated fatty acids can be converted to esters (such as their ethyl ester) or salts (such as their lithium, sodium, calcium, magnesium salts and the like), by processes well known to one of ordinary skill in the art.

The process of this invention permits the production of compositions comprising at least 70% by weight of long chain monounsaturated fatty acids. Preferably, such compositions have LC-MUFA concentrations of more than 75%, more preferably of higher than 80% by weight. Such $C_{20}$-$C_{22}$ long chain monounsaturated fatty acids may be in the form of free fatty acids, monoesters (preferably ethyl esters), triglycerides or mixtures thereof.

EXAMPLES

The following examples are provided to illustrate the invention in accordance with the principles of this invention, but are not to be construed as limiting the invention in any way except as indicated in the appended claims.

In the following Examples, except as indicated otherwise, herring oil having the composition listed below was employed as the starting fish oil material:

TABLE 1

Fatty acid composition of herring oil employed as analyzed by gas chromatography

| Fatty acid | Percent Area |
| --- | --- |
| C14:0 | 8.2 |
| C14:1 | 0.1 |
| C16:0 | 12.6 |
| C16:1n7 | 4.7 |
| C16:4n1 | 0.4 |

TABLE 1-continued

Fatty acid composition of herring oil employed as analyzed by gas chromatography

| Fatty acid | Percent Area |
|---|---|
| C18:0 | 0.9 |
| C18:1n9 | 11.1 |
| C18:1n7 | 1.4 |
| C18:2n6 | 1.3 |
| C18:3n3 | 0.8 |
| C18:4n3 | 2.5 |
| C20:0 | 0.1 |
| C20:1n11 | 1.1 |
| C20:1n9 | 13.3 |
| C20:1n7 | 0.3 |
| C20:2n6 | nd |
| C20:3n3 | nd |
| C20:4n6 | 0.1 |
| C20:4n3 | 0.4 |
| C20:5n3 (EPA) | 6.3 |
| C21:5n3 | 0.3 |
| C22:1(n13 + n11) | 22.2 |
| C22:1n9 | 1.3 |
| C22:1n7 | nd |
| C22:5n6 | nd |
| C22:5n3 | 0.5 |
| C22:6n3 (DHA) | 6.2 |
| C24:1 | 0.8 | nd: not observed

Example 1

Two Step Fractionation: First Fractionation Step in Order to Remove Saturated Fatty Acids 1000 grams of free fatty acids (FFA) from hydrolyzed herring oil from Table 1 was dissolved in 2 liters of acetone. After addition of 100 ml 5 M LiOH (corresponding to 3.5 g lithium ions, or 0.35 weight % relative to the starting fatty acids) and stirring overnight at 40° C., 2 additional liters of acetone were added, and the reaction mixture was cooled in an ice bath for 4 hours. The precipitate that was formed was enriched in saturated fatty acids and removed by filtration and discarded.

The filtrate was acidified with citric acid and part of the acetone was removed on a rotary evaporator under vacuum in order for the free fatty acids to form a separate phase from the remaining acetone/aqueous solution. The free fatty acids were removed using a separatory funnel and washed with several portions of water until a pH of 5-6 was obtained. The free fatty acid phase was then treated under vacuum in a rotary evaporator until a stable weight was obtained. 798.5 g free fatty acids were isolated in this way. The fatty acid composition of this fraction is shown in Table 2. After analyses this free fatty acid mixture (786.7 g) was dissolved in 1.6 liters of acetone. LiOH (472 ml 5M, corresponding to 16.4 g lithium ions, or 2.1 weight % relative to the free fatty acids) was added during stirring. After stirring for 40° C. overnight, an additional 1.6 liters of acetone was added, and the reaction mixture was cooled in an ice bath for 4 hours and filtered.

The acetone filtrate was acidified using citric acid and the free fatty acid triglyceride omega-3 concentrate (185 gram) was isolated using the procedure described above. The fatty acid composition of the concentrate is shown in Table 2.

The filtrate, containing the isolated lithium salts, was recrystallized from ethanol. After acidification of the recrystallized salts, 373 g of MUFA-rich concentrate was obtained. The fatty acid composition of the MUFA concentrate after recrystallization is shown in Table 2.

TABLE 2

Concentrations analyzed by gas chromatography (percent area)

| Fatty acid | Omega-3 concentrate | MUFA-concentrate after recrystallization |
|---|---|---|
| 14:0 | 1.1 | 9.0 |
| 14:1 | 0.1 | 0.0 |
| 16:0 | 0.4 | 10.9 |
| 16:1 | 6.5 | 2.9 |
| 18:0 | — | 0.6 |
| 18:1n9 | 9.0 | 9.8 |
| 18:1n7 | 0.4 | 1.9 |
| 18:3n3 | 2.0 | 0.3 |
| 18:4n3 | 10.6 | — |
| 20:0 | — | — |
| 20:1n11 | 0.4 | — |
| 20:1n9 | 1.1 | 22.0 |
| 20:1n7 | — | 0.4 |
| 20:4n3 | 1.5 | — |
| EPA | 26.4 | 0.3 |
| 22:1n11 + 13 | 0.8 | 35.9 |
| 22:1n9 | — | 1.9 |
| 22:1n7 | — | 0.2 |
| 21:5n3 | 1.0 | — |
| 22:5n3 | 2.0 | — |
| DHA | 25.79 | 0.3 |
| 24:1 | — | 0.8 |

The recrystallized MUFA concentrate was distilled twice a by using a laboratory short path distillation still (Leybold KDL 4). At the first distillation (120° C., $10^{-4}$–$10^{-3}$ mbar) a distillate of 28.3% was discarded in order to remove fatty acids of low chain length. The residue from this distillation was distilled at 185° C., and gave as product a distillate of 80.6% (165.8 g). The FFA concentrate was transformed into triglycerides using enzyme catalyzed esterification with glycerol. The acid composition of the MUFA-concentrate as triglycerides is shown in Table 3. The skilled person knows that the enzyme catalyzed esterification step has no effect on the fatty acid composition, and so Table 3 also represents the fatty acid composition of the FFA concentrate.

TABLE 3

Fatty acid composition of TG concentrate of LC-MUFA from herring oil. The analysis is performed using a gas chromatography temperature gradient similar to that described in the Ph. Eur. monograph number 1192 for cod liver oil.

| Fatty acid | Concentration (GC A %) |
|---|---|
| C14:0 | 1.7 |
| C14:1 | 0.1 |
| C16:0 | 5.2 |
| C16:1 | 1.3 |
| C18:0 | 0.7 |
| C18:1 n-9 | 8.5 |
| C18:1 n-7 | 1.7 |
| C18:2 n-6 | 0.5 |
| C18:3 n-3 | 0.3 |
| C18:4 n-3 | 0.1 |
| C20:1 n-11 | 1.3 |
| C20:1 n-9 | 24.7 |
| C20:1 n-7 | 0.5 |
| C20:2 n-6 | 0.3 |
| C20:3 n-3 | 0.1 |
| C20:4 n-6 | 0.1 |
| C20:4 n-3 | 0.1 |
| C20:5 n-3 (EPA) | 0.4 |
| C22:1 n-11 | 46.1 |
| C22:1 n-9 | 2.2 |
| C22:1 n-7 | 0.2 |
| C22:5 n-3 | 0.1 |
| C22:6 n-3 (DHA) | 0.4 |
| C24:1 | 1.4 |

The MUFA triglyceride product had a completely neutral taste and no observable odor. The skilled person will realize that if needed, deodorization procedures could be used in order to further improve the sensory characteristics of the product. Quality characteristics of the concentrate are given in Table 4.

The skilled person knows that the enzymatically catalyzed esterification cannot alter the content of unsaponifiable (UFS) matter or cholesterol in the sample. The reduction of these two characteristics compared to the starting oil (78 and 96% respectively) is caused by the fatty acid fractionation process. Thus, the present process is not only effective in order to produce very high concentrates of MUFA, but also to produce such concentrates that are very low in UFS, including cholesterol.

Due to their lipophilic character, the pollutants like DDT, PCB, dioxins and PBDE are envisaged to follow the UFS fraction to the same degree as cholesterol. The MUFA concentrates obtained according to the present invention are therefore considered to be unique in the sense that they provide valuable LC-MUFA without the toxic environmental pollutants which accompany these fatty acids in the normal diet. Table 4 also shows that the product has a very low content of oxidation products.

TABLE 4

Composition of triglyceride (TG) concentrate of MUFA..
MUFA TG90 from herring oil

| Analysis | Unit | Result |
|---|---|---|
| Appearance | Clear oil | Clear Oil |
| Acid Value | mg KOH/g | 0.1 |
| Cholesterol | mg/g | 0.2[1] |
| Unsaponifiable matter | % | 0.2[2] |
| Colour | Gardner | 1 |
| Peroxide value | meq/kg | 0.2 |
| Anisidine value | — | 1 |
| Total oxidation | | 1 |
| Absorbance 233 nm | AU | 0.06 |
| Triglycerides | A %[3] | 90.1 |
| Diglycerides | A %[3] | 9.5 |
| Monoglycerides | A %[3] | 0.3 |
| Fatty acids/ethyl ester | A %[3] | 0.1 |
| Oligomers | A %[3] | 0.0 |

[1]Cholesterol in starting oil: 6.5 mg/g
[2]UFS in starting oil: 0.9%
[3]As analyzed by gel permeation chromatography The resultant MUFA product as well as the starting fish oil material were analyzed for their persistent organic pollutant contents. The results of such analyses are presented in Table 4A Below:

TABLE 4A

| Persistent organic pollutant (POP) group | Starting herring oil | MUFA TG90 (percent reduction) | EU regulations for marine oils used as food[2] |
|---|---|---|---|
| 7PCB[1] (mg/g) | 0.053 | 0.0008 (98) | Max. 0.200[3] |
| Dioxin-like PCBs (TE WHO, pg/g) | 3.98 | <0.15 (>96) | — |
| Dioxins + furans (TE WHO, pg/g) | 3.36 | <0.42 (>87) | Max. 1.75 |
| Dioxin-like PCBs + dioxins/furans (TE WHO, pg/g) | 7.25 | <0.57 (>92) | Max. 6.0 |

[1]7PCB: Sum of PCB congeners 28, 52, 101, 118, 138, 153 and 180, often referred to as a measure for the sum of non-dioxin-like PCBs.
[2]Commission Regulation (EU) No 1259/2011 of 2 Dec. 2011
[3]The EU regulation only utilises the sum of PCB congeners 28, 52, 101, 138, 153 and 180; i.e. congener 118 is not included in the sum.

It is well known that North Atlantic herring oils contain higher levels of POP than the South American fish oils that normally are utilized for the production of omega-3 concentrates. Despite this, when using such herring oil as starting oil, and without using any pre-treatment of the oil in order to reduce the content of POP, the present invention enables the manufacture of MUFA products that are very low in such pollutants. Typically, the POP-levels are reduced by more than 90% compared to the starting material. In the above example the starting herring oil did not comply with EU limits for POP in marine oils used as food, while the MUFA triglyceride product had a POP content far below those limits.

Example 2

1352.5 g free fatty acids from herring oil of Table 1 was dissolved in 710 ml acetone ml 36 ml 5 M LiOH (aq) and stirred overnight at 40° C. before the reaction mixture was placed in an ice bath for 4 hours. The precipitate that was formed was enriched in saturated fatty acids, and was removed by filtration and discarded. After acidification with citric acid 223.5 g of a free fatty acid oil was recovered using the procedure as described in Example 1.

50 g of this oil was subjected to further fractionation step by stirring overnight with 200 ml acetone and 35 ml LiOH (aq) before the reaction mixture was placed in an ice bath for 4 hours. The precipitate that was formed was filtered. Acidification of the filtrate with aqueous citric acid and isolation as in Example 1 gave a MUFA concentrate (34.1 g) with composition as shown by Table 5 (product 2a). Acidification of the filtrate and work-up according to the procedure of Example 1 resulted in the recovery of an omega-3 concentrate with composition as shown in Table 5, product 2b. The skilled person knows that these concentrates could be further purified, for example by using short path distillation and recrystallization as described above. (SFA=saturated fatty acids)

TABLE 5

Results from a two-step lithium fractionation.
Results in GC Area %.

| | Omega3 | SFA | MUFA | EPA | DHA |
|---|---|---|---|---|---|
| MUFA-concentrate (product 2a): Fatty acids obtained from lithium salts. Yield from step 1: 68% | 6.9 | 15.1 | 73.4 | 2.4 | 2.1 |
| Omega-3-concentrate (product 2b): Fatty acids obtained from filtrate after removal of lithium salts. Yield from step 1: 15% | 80.2 | 1.8 | 7.6 | 30.4 | 31.2 |

Example 3

Fractionation on Distilled Ethyl Esters of Herring Oil

The content of saturated fatty acids in the ethyl esters of the herring oil of Table 1 was reduced by using a laboratory short path distillation still (Leybold KDL 4) to distil off short chain fatty acids (including the saturated C14:0 and C16:0) at 91° C. and a pressure of $10^{-4}$ mbar. The distillate (30% by weight) was discarded. The residue from the distillation had a fatty acid composition as given in Table 6

850 grams of the residue from the distillation was dissolved in 1700 ml acetone. The mixture was stirred during the addition of 520 ml 5M aqueous KOH, 1280 ml 5 M aqueous LiOH and a further amount of 1700 ml acetone. After stirring overnight at 40° C., the reaction mixture was placed in an ice bath for approx. 4 hours.

After filtering, the filtrate was acidified to transform the dissolved fatty acid salts into free fatty acids. The composition of the recovered fatty omega-3 rich fatty acids (182 g) is given in Table 6.

A two-step short path distillation of the recovered ethyl esters was then performed in order to remove light and heavy by-products: First distillation step: 130° C. and $10^{-4}$ mbar. Distillate approx. 11%, residue approx. 89%. The second distillation step was conducted on the residue from the first step: 182° C. and $10^{-4}$ mbar. Distillate approx. 97.8%. Residue approx. 2.2%.

The final distillate of 150.6 g was enriched in omega-3 acids. The composition of the distilled omega-3 concentrate is given in Table 6. The omega-3 concentrate contained 78% omega-3 acids. The skilled person knows than the concentration could be increased further according to known technologies.

The precipitate from the filtration weighed 1890 g, after most of the solvent had been removed by a flow of nitrogen. 100 g of this material was recrystallized in 100 ml ethanol (96%). The recrystallized lithium salts were acidified with citric acid and 22.7 g of a concentrate of MUFA free fatty acids was recovered. This corresponds to a concentrate of 429 g, if all the material had been recrystallized.

The fatty acid composition of the MUFA concentrate, before and after recrystallization, is given in Table 6. The recrystallized MUFA concentrate had a content of 88% MUFA and only 0.1% omega-3-acids (reduced from 4.5% before recrystallisation). The latter characteristic is important in order to avoid any development of rancidity and "fishy" odor from the product.

Example 4

Fractionation on Distilled Ethyl Esters of Herring Oil Using Ethanol as a Solvent The same batch of starting material (ethylated herring oil where short chain fatty acids have been removed by distillation) was used in Example 4 as in Example 3. Example 4 started with 100 g ethyl ester instead of 850 ml in Example 3. In order to be able to compare with Example 3 the volumes of reagents and solvents were reduced in approximately the same ratio (200+200 ml ethanol (96%), 60 ml 5M KOH, 160 ml 5M LiOH). The reaction conditions were otherwise as in Example 3.

After removal of the lithium salts by filtration, 29.1 g free fatty acids were obtained after acidification of the ethanol solution. Acidification of the precipitated salts resulted in the isolation of 44.6 g free fatty acids (fatty acid salt not recrystallized). The fatty acid composition of the two products can be seen in Table 7.

TABLE 6

Fatty acid analyses Example 3 (Gas Chromatography Area %)

| Fatty acid | Fatty acid content starting ethyl ester (after removal of short chain fatty acids by distillation) | Omega-3 concentrate before distillation | Omega-3 concentrate after a two step short path distillation | MUFA concentrate before recrystallisation | MUFA concentrate after recrystallisation |
|---|---|---|---|---|---|
| 14:0 | 0.5 | 0.1 | 0.1 | 0.6 | 0.4 |
| 14:1 | — | — | — | — | — |
| 16:0 | 5.9 | 0.4 | 0.3 | 7.4 | 8.1 |
| 16:1 | 1.7 | 2.9 | 2.2 | 1.4 | 0.2 |
| 18:0 | 0.9 | — | — | 1.2 | 1.6 |
| 18:1n9 | 10.6 | 9.5 | 9.0 | 10.8 | 2.5 |
| 18:1n7 | 1.4 | 0.4 | 0.4 | 1.6 | 1.2 |
| 18:3n3 | 0.8 | 2.1 | 2.0 | 0.4 | — |
| 18:4n3 | 2.3 | 8.2 | 7.6 | 0.5 | — |
| 20:1n11 | 1.7 | 0.5 | 0.6 | 24.0 | 26.7 |
| 20:1n9 | 18.0 | 1.0 | 1.1 | 0.3 | — |
| 20:1n7 | 0.4 | — | — | — | — |
| 20:4n3 | 0.6 | 1.8 | 2.0 | 0.1 | — |
| EPA | 8.2 | 29.1 | 29.6 | 1.7 | — |
| 22:1n11 + 13 | 30.6 | 0.6 | 0.5 | 41.0 | 53.7 |
| 22:1n9 | 1.6 | — | — | 2.4 | 2.5 |
| 22:1n7 | — | — | — | — | — |
| 21:5n3 | 0.4 | 1.3 | 1.3 | 0.3 | — |
| 22:5n3 | 0.8 | 2.7 | 2.9 | 0.2 | — |
| DHA | 8.5 | 31.5 | 33.0 | 2.1 | 0.1 |
| 24:1 | 1.2 | — | — | 1.5 | 1.8 |

From the results we see that fractionation in ethanol gives a MUFA-concentrate that is richer in LC-MUFA than fractionation using the same volumes of acetone. Unexpectedly, C18:1 precipitated to a lesser extent when ethanol is used as solvent compared to the same volume of acetone.

This gives as the second product an omega-3 concentrate which also contains substantial amounts of oleic acid (C18:1n9), the recognized valuable fatty acid from the Mediterranean diet. Thus, fractionation in ethanol can give a concentrate enriched in the beneficial omega-3 acids and oleic acid, plus another concentrate enriched in LC-MUFA.

TABLE 7

Fatty acid analyses Example 4 (Gas Chromatograph Area %)

| Fatty acid | Fatty acid content starting ethyl ester (after removal of short chain fatty acids by distillation) | Omega-3 concentrate | MUFA concentrate |
|---|---|---|---|
| 14:0 | 0.5 | 0.8 | 0.8 |
| 14:1 | — | — | — |
| 16:0 | 5.9 | 1.7 | 9.5 |
| 16:1 | 1.7 | 4.7 | 0.8 |
| 18:0 | 0.9 | — | 1.4 |
| 18:1n9 | 10.6 | 20.2 | 6.1 |
| 18:1n7 | 1.4 | 1.2 | 1.5 |
| 18:3n3 | 0.8 | 1.9 | 0.2 |
| 18:4n3 | 2.3 | 6.2 | 0.4 |
| 20:1n11 | 1.7 | 2.1 | 1 |
| 20:1n9 | 18.0 | 3.4 | 24 |
| 20:1n7 | 0.4 | — | 0.5 |
| 20:4n3 | 0.6 | 1.3 | — |
| EPA | 8.2 | 19.9 | 1.3 |
| 22:1n11 + 13 | 30.6 | 6.7 | 45.2 |
| Ple | 1.6 | — | 2.2 |
| 22:1n7 | — | — | — |
| 21:5n3 | 0.4 | 0.9 | — |
| 22:5n3 | 0.8 | 1.8 | 0.1 |
| DHA | 8.5 | 20.8 | 1.7 |
| 24:1 | 1.2 | — | 1.7 |

Example 5

Fractionation on Distilled Ethyl Esters of Herring Oil Using Ethanol as a Solvent The content of saturated fatty acids in the ethyl esters of the herring oil of Table 8 was reduced in a similar manner as described in Example 3, using a pilot plant equipment for short path distillation (VTA, model VK83-6-SKR-G with degasser). The distillation took place at a temperature of 113° C. and a flow of 7.4 kg/h and a vacuum of 0.01 mbar. The composition of ethyl esters after removal of short chain fatty acids is given in Table 8, together with the fatty acid composition of the resulting MUFA concentrate.

The MUFA concentrate was obtained in the following manner:
After removal of short chain fatty acid ethyl esters, portions of about 50 g of the non-distilled residue were mixed with 50 ml 96% ethanol and:
  A: 25 ml 5 M KOH (aqueous solution) and 65 ml 5M LiOH (aqueous solution), corresponding to 45 g calculated as lithium per kg of the ethyl ester composition that was used for fractionation.
  B: 15 ml 5 M KOH (aqueous solution) and 75 ml 5M LiOH (aqueous solution), corresponding to 52 g calculated as lithium per kg of ethyl ester composition.
  C: 5 ml 5 M KOH (aqueous solution) and 85 ml 5M LiOH (aqueous solution), corresponding to 59 g calculated as lithium per kg of ethyl ester composition.
The reaction mixtures were stirred at 40° C. for 2 hours and cooled in an ice bath. For practical reasons the cooling lasted overnight.
The precipitates were removed by filtration. HCl (4 M) was added for acidification, and the resulting mixtures were gently heated during stirring in order for separation a liquid free fatty acid phase to take place. The free fatty acid phases were treated under vacuum in a rotary evaporator to remove traces of water. The products were analysed by GC. The results are given in Table 8.

Yields (calculated from an average chain length of C20 for the starting ethyl ester mixture, which gives 92% as theoretical yield from hydrolysis to free fatty acids):
  A: 25.9 g (56% based on 50.6 g ethyl esters as starting material)
  B: 27.4 g (60% based on 49.8 g ethyl esters as starting material)
  C: 25.3 g (55% based on 50.3 g ethyl esters as starting material)

After removal of the precipitate, the filtrates were acidified with 4M HCl (4M). Gentle heating during stirring was applied in order to obtain a liquid free fatty acid phase. The free fatty acid phase was washed with a small amount of water, and thereafter the free fatty acid phase was dries in a rotary evaporator. The composition of the resulting concentrates of omega-3-acids plus oleic acid (C18:1n9) are given in Table 8.

Yields (calculated from an average chain length of C20 for the starting ethyl ester mixture, which gives 92% as theoretical yield from hydrolysis to free fatty acids):
  A: 11.5 g (25% based on 50.6 g ethyl esters as starting material)
  B: 8.7 g (19% based on 49.8 g ethyl esters as starting material)
  C: 9.1 g (20% based on 50.3 g ethyl esters as starting material)

Regarding yields it may be noted that the artisan will realize that for small amounts of material loss during transfer of intermediates and products will be greater on a per cent basis than when the same reaction takes place in large scale equipment.

As can be seen from the Table, the composition of the MUFA concentrates does not vary greatly between experiments A, B, C. As discussed in the specification and in Example 1, recrystallization of the precipitated lithium salts before acidification and separation of the resulting free acids would have increased the MUFA content and reduced the PUFA content of these MUFA concentrates.

For the PUFA concentrates that were formed simultaneously with the MUFA concentrates there can be observed a significant increase in the concentration of omega-3 acid with increasing amounts of lithium ions as precipitating agent. In contrast to this, the concentration of omega-6 acids remains surprisingly constant with increasing amounts of lithium. This is in contrast to the common use of urea fractionation for the formation of PUFA concentrates. During urea fractionation unfortunately the omega-6 acids are concentrated more than the corresponding omega-3 acids. Thus, lithium fractionation surprisingly can be utilised to manufacture PUFA concentrates with a higher, and thus more beneficial, omega-3/omega-6 ratio than what can be obtained with urea fractionation.

TABLE 8

Results in GC area %.

| Fatty acid | Ethylated herring oil used in example 5 | Ethyl ester composition after removal of short chain fatty acids by distillation | MUFA concentrate (free fatty acids) A | B | C | PUFA concentrate (free fatty acids) A | B | C |
|---|---|---|---|---|---|---|---|---|
| C14:0 | 7.3 | 0.6 | 0.7 | 0.7 | 0.7 | 0.3 | 0.3 | 0.2 |
| C14:1 | 0.3 | 0.0 | 0.0 | 0.1 | 0.0 | 0.1 | 0.0 | 0.0 |
| C16:0 | 12.4 | 6.4 | 8.4 | 8.0 | 7.9 | 1.7 | 1.5 | 1.1 |
| C16:1n7 | 5.0 | 2.1 | 1.5 | 1.6 | 1.6 | 3.9 | 3.6 | 3.3 |
| C16:4n1 | 0.5 | 0.2 | 0.1 | 0.1 | 0.1 | 0.4 | 0.4 | 0.5 |
| C18:0 | 1.0 | 0.9 | 1.3 | 1.2 | 1.2 | 0.1 | 0.0 | 0.0 |
| C18:1n9 | 10.8 | 10.6 | 8.1 | 9.3 | 9.7 | 16.2 | 14.1 | 12.4 |
| C18:1n7 | 1.4 | 1.4 | 1.6 | 1.6 | 1.6 | 0.8 | 0.7 | 0.6 |
| C18:2n6 | 1.4 | 1.2 | 0.7 | 0.8 | 0.8 | 2.6 | 2.6 | 2.5 |
| C18:3n3 | 0.9 | 0.8 | 0.5 | 0.5 | 0.5 | 1.8 | 1.8 | 1.8 |
| C18:4n3 | 2.6 | 2.3 | 1.0 | 1.1 | 1.0 | 5.7 | 6.2 | 6.6 |
| C20:1n11 | 1.1 | | | | | | | |
| C20:1n9 | 12.7 | 17.7* | 22.0* | 21.5* | 21.7* | 4.0* | 3.1* | 2.4* |
| C20:1n7 | 0.3 | 0.4 | 0.5 | 0.4 | 0.5 | 0.2 | 0.1 | 0.1 |
| C20:2n6 | 0.2 | 0.2 | 0.2 | 0.2 | 0.2 | 0.2 | 0.2 | 0.2 |
| C20:3n3 | 0.1 | 0.1 | 0.1 | O.1 | 0.1 | 0.1 | 0.1 | 0.1 |
| C20:4n6 | 0.2 | 0.2 | 0.1 | 0.0 | 0.0 | 0.5 | 0.6 | 0.6 |
| C20:4n3 | 0.5 | 0.5 | 0.2 | 0.3 | 0.2 | 1.4 | 1.4 | 1.6 |
| C20:5n3 (EPA) | 6.9 | 8.4 | 3.5 | 3.9 | 3.6 | 21.0 | 22.7 | 24.5 |
| C21:5n3 | 0.3 | 0.4 | 0.1 | 0.2 | 0.2 | 0.9 | 1.0 | 1.1 |
| C22:1(n13 + n11) | 21.3 | 29.7 | 39.0 | 37.6 | 37.9 | 3.8 | 3.0 | 2.2 |
| C22:1n9 | 1.3 | 1.9 | 2.5 | 2.2 | 2.3 | 0.9 | 0.4 | 0.3 |
| C22:1n7 | 0.2 | 0.2 | 0.3 | 0.3 | 0.3 | 0.3 | nd | nd |
| C22:5n6 | 0.1 | 0.1 | 0.1 | 0.1 | 0.1 | 0.3 | 0.4 | 0.4 |
| C22:5n3 | 0.6 | 0.8 | 0.3 | 0.4 | 0.4 | 2.0 | 2.1 | 2.3 |
| C22:6n3 | 7.0 | 9.5 | 3.8 | 4.3 | 3.9 | 23.8 | 25.9 | 28.0 |
| C24:1 | 0.8 | 1.0 | 1.4 | 1.3 | 1.4 | 0.2 | 0.2 | 0.1 |

*including C20:1n11

Example 6

Direct Fractionation of Fish Oil

Because of the very complex fatty acid composition of marine oils, high concentrates of long-chain omega-3 fatty acids can in commercial scale not easily be obtained by any single fractionation technique. Commercial production of omega-3 concentrates starts with transesterification of the oil with ethanol, or by hydrolysing the oil to free fatty acids or their salt. Contrary to this practise, the fish oil itself can be used directly as starting material for the present process.

49.4 g of the herring oil (i.e. the original oil in TG form) of Table 1 was dissolved in 100 ml ethanol (96%). During stirring 30 ml 5 M KOH was added, followed by 40 ml 5 M LiOH and a further amount of 100 ml ethanol (96%). The reaction was stirred overnight at 40° C. and thereafter cooled 4 hours in an ice bath before filtering. Fatty acid concentrates were isolated from the precipitated lithium salts and the dissolved potassium/lithium salts in the same manner as described in the examples above.

The composition of the products were as shown in Table 9. Similar to the examples above, recrystallization of the lithium salt LC-MUFA concentrate can reduce the omega-3 content to levels below 1%. As it is impossible to fractionate a triglyceride oil like fish oil using distillation, it can be observed that the two initial concentrates contain more short chain fatty acids than concentrates produced from pre-distilled starting materials. However, the skilled person will realize that by a further treatment of the concentrates of Table 9 the content of C14 and C16 fatty acids can be reduced using short path distillation or other known techniques.

TABLE 9

| | LC-MUFA concentrate | Omega-3 plus oleic acid (C18:1n9) concentrate |
|---|---|---|
| 14:0 | 9.7 | 5.0 |
| 16:0 | 18.3 | 1.7 |
| 16:1 | 1.9 | 11.0 |
| 16:4n1 | 0.1 | 0.8 |
| 18:0 | 1.3 | — |
| 18:1n9 | 5.5 | 23.6 |
| 18:1n7 | 1.4 | 1.1 |
| 18:2n6 | 0.5 | 2.7 |
| 18:3n3 | 0.3 | 1.6 |
| 18:4n3 | 0.7 | 6.3 |
| 20:1n11 | 17.9 | 5.4 |
| 20:1n9 | 0.4 | — |
| 20:4n3 | 0.1 | 0.6 |
| 20:5n3 | 1.8 | 16.12 |
| 22:1n11 + 13 | 32.1 | 3.3 |
| 22:1n9 | 1.9 | — |
| 22:1n7 | 0.2 | — |
| 21:5n3 | — | 0.3 |
| 22:5n3 | 0.2 | 0.9 |
| 22:6n3 | 1.9 | 15.3 |
| 24:1 | 1.16 | — |

What is claimed is:

1. A method for obtaining an enriched composition of $C_{20}$-$C_{22}$ long chain monounsaturated fatty acids comprising the steps of:
   a) mixing an oil composition comprising $C_{20}$-$C_{22}$ long chain polyunsaturated fatty acids and at least 15% by weight $C_{20}$-$C_{22}$ long chain monounsaturated fatty acids with (i) an organic solvent selected from the group consisting of $C_1$-$C_5$ alcohols and ketones of the formula $R^1(C{=}O)R^2$ wherein $R^1$ and $R^2$ are each independently $C_1$-$C_5$ alkyl; and (ii) a lithium salt to form a mixed composition comprising the lithium salts of long chain monounsaturated fatty acids and the lithium salts of the long chain polyunsaturated fatty acids at 55° C. to 80° C.;

b) reducing the temperature of the mixed composition formed in step a such that the lithium salts of the long chain monounsaturated fatty acids form a precipitate; and c) removing the precipitate to obtain an enriched composition of long chain monounsaturated fatty acids.

2. The method of claim 1, wherein the oil composition is derived from fish, crustaceans, algae, plankton or higher plants.

3. The method of claim 1, wherein the oil composition is comprised of a member selected from the group consisting of free fatty acids and fatty acid monoesters.

4. The method of claim 3, wherein the fatty acid monoesters comprise ethyl esters.

5. The method of claim 1, wherein the oil composition has been subjected to a prior fractionation step to reduce the concentration of at least one of saturated fatty acids and shorter chain fatty acids.

6. The method of claim 1, wherein an additional base is added in step a.

7. The method of claim 6, wherein said additional base is potassium hydroxide.

8. The method of claim 1, wherein the organic solvent is selected from the group consisting of ethanol and acetone.

9. The method of claim 1, wherein the solvent is added in an amount of between 0.5 and 8 liters per kilogram of oil composition.

10. The method of claim 1, wherein the lithium salt is selected from the group consisting of lithium carbonate, lithium bicarbonate and lithium hydroxide.

11. The method of claim 10, wherein the lithium salt comprises lithium hydroxide.

12. The method of claim 1, wherein the lithium salt is added in an amount of between 5 and 70 grams, calculated as lithium, per kilogram of oil composition.

13. The method of claim 1, wherein the mixed composition is cooled to 10° C. or less in step b.

14. The method of claim 1, wherein the oil composition is a fish oil composition.

15. The method of claim 1, wherein the content of persistent organic environmental pollutants, as measured by the content of PCBs, is reduced by more than 90% compared to the starting oil composition.

16. A composition comprising at least 70% by weight $C_{20}$-$C_{22}$ long chain monounsaturated fatty acids.

17. The composition of claim 16 wherein said composition comprises at least 80% by weight $C_{20}$-$C_{22}$ long chain monounsaturated fatty acids.

18. The composition of claim 16 wherein said composition comprises free $C_{20}$-$C_{22}$ long chain monounsaturated fatty acids.

19. The composition of claim 16 wherein said composition comprises monoesters of $C_{20}$-$C_{22}$ long chain monounsaturated fatty acids.

20. The composition of claim 16 wherein said composition comprises triglycerides of $C_{20}$-$C_{22}$ long chain monounsaturated fatty acids.

* * * * *